United States Patent
Bergeron

(10) Patent No.: US 6,299,634 B1
(45) Date of Patent: Oct. 9, 2001

(54) MODULAR BIFURCATED VASCULAR PROSTHESIS

(76) Inventor: Patrice Bergeron, 38, Boulevard Lei Roure, 13009 Marseille (FR)

(*) Notice: Subject to any disclaimer, the term of this patent is extended or adjusted under 35 U.S.C. 154(b) by 0 days.

(21) Appl. No.: 09/200,323

(22) Filed: Nov. 25, 1998

Related U.S. Application Data

(63) Continuation-in-part of application No. PCT/FR97/00931, filed on May 28, 1997.

(30) Foreign Application Priority Data

May 28, 1996 (FR) ................................ 96/06557

(51) Int. Cl.⁷ ...................................... A61F 2/06
(52) U.S. Cl. ............................. 623/1.1; 623/1.35
(58) Field of Search .................... 623/1.1, 1.12, 623/1.13, 1.15, 1.35; 606/194, 192, 198

(56) References Cited

U.S. PATENT DOCUMENTS 5,824,040 * 10/1998 Cox et al. ................................ 623/1

FOREIGN PATENT DOCUMENTS

| 0 646 365 A | 5/1995 | (EP) . |
| 0 686 379 A2 | 12/1995 | (EP) . |
| 2 722 678 | 1/1996 | (FR) . |
| 2722678 * | 1/1996 | (FR) ................................ A61F/2/06 |
| WO 95/21592 | 8/1995 | (WO) . |
| WO95/21592 * | 1/1996 | (WO) ................................ A61F/2/06 |
| WO 96/24306 | 8/1996 | (WO) . |

\* cited by examiner

*Primary Examiner*—Gene Mancene
*Assistant Examiner*—Eduardo C. Robert
(74) *Attorney, Agent, or Firm*—Schnader Harrison Segal & Lewis LLP

(57) ABSTRACT

A bifurcated vascular prosthesis including a tubular main branch extended by at least two sub-branches, wherein at least one part of the main branch has an expandable strengthener in the form of an expandable annular section; and each sub-branch has at least one expandable zone longitudinally offset to avoid overlapping of corresponding longitudinally offset expandable zones between sub-branches.

11 Claims, 3 Drawing Sheets

MODULAR BIFURCATED VASCULAR PROSTHESIS

This application is a Continuation-in-Part of PCT/FR97/00931, filed May 28, 1997.

FIELD OF THE INVENTION

This invention features vascular prostheses designed to treat aortic aneurisms via the endoluminal route. The endovascular prostheses currently proposed are designed, in a first embodiment, for repairs, by means of a straight prosthetic tube attached at either end by an endoprosthesis. In another known embodiment, the repair is achieved by means of an aortic bifurcation whose form is similar to that of the anatomical layout.

BACKGROUND

In the prior art, an expanding prosthesis is also known, described in the French patent FR2678508. This document describes a device for reinforcing vessels in the human body, of the type which has an extended strengthener which runs along the inside of the vessel to be reinforced. In the invention, in order to allow unbroken junctions to be formed especially at the bifurcations, at least two devices are used with self-locking spirals which allow unbroken junctions to be created.

Another document of the prior art, published under the number EP508473 describes a bifurcated endovascular prosthesis, formed by a main branch and flexible sub-branches. The drawback with this type of prosthesis which is the closest state of the art is that to make surgical implantation possible, numerous models are required to suit the diameters and lengths of the aorta and the iliac arteries.

SUMMARY OF THE INVENTION

The purpose of this invention is to overcome these drawbacks and to offer a prosthesis whereby one model can be adapted to suit a wide range of vascular sections. Another objective is to offer a prosthesis which can be surgically implanted rapidly, in order to reduce the length and cost of the operation.

To this end, the invention features first of all a bifurcated vascular prosthesis, formed by a tubular main branch and extended by means of two tubular sub-branches, characterised in that at least one part of the main branch has expandable strengtheners.

The main branch will preferably be made from an expandable material, such as PTFE, reinforced by an expandable annular section.

The inlet of the main branch is advantageously formed of a stripped reinforced tubular section wherein a part of the expandable material (PTFE) has been stripped away to reveal the reinforcing material. This stripped section provides better adherence for the prosthesis.

In a first embodiment, the sub-branches are free and not reinforced. The main branch is advantageously expandable up to a diameter of around 28 mm, and the sub-branches are conically shaped, the end of which measures approximately 10 mm in diameter.

In a second embodiment, the main branch is extended by means of two reinforced sub-branches which are expandable up to a diameter of 10 mm, the expandable zones being offset longitudinally, and the sub-branches being of different lengths in order to avoid the reinforced zones overlapping.

Advantageously in both embodiments, the sub-branches are each extended by means of expandable reinforced annular sections, the length of which can be adjusted to suit the distal attachment to the iliac arteries.

BRIEF DESCRIPTION OF THE DRAWINGS

The description will become clearer upon reading the following description, referring to the non-restrictive examples of embodiments, where.

DETAILED DESCRIPTION OF THE INVENTION

Figure 1:
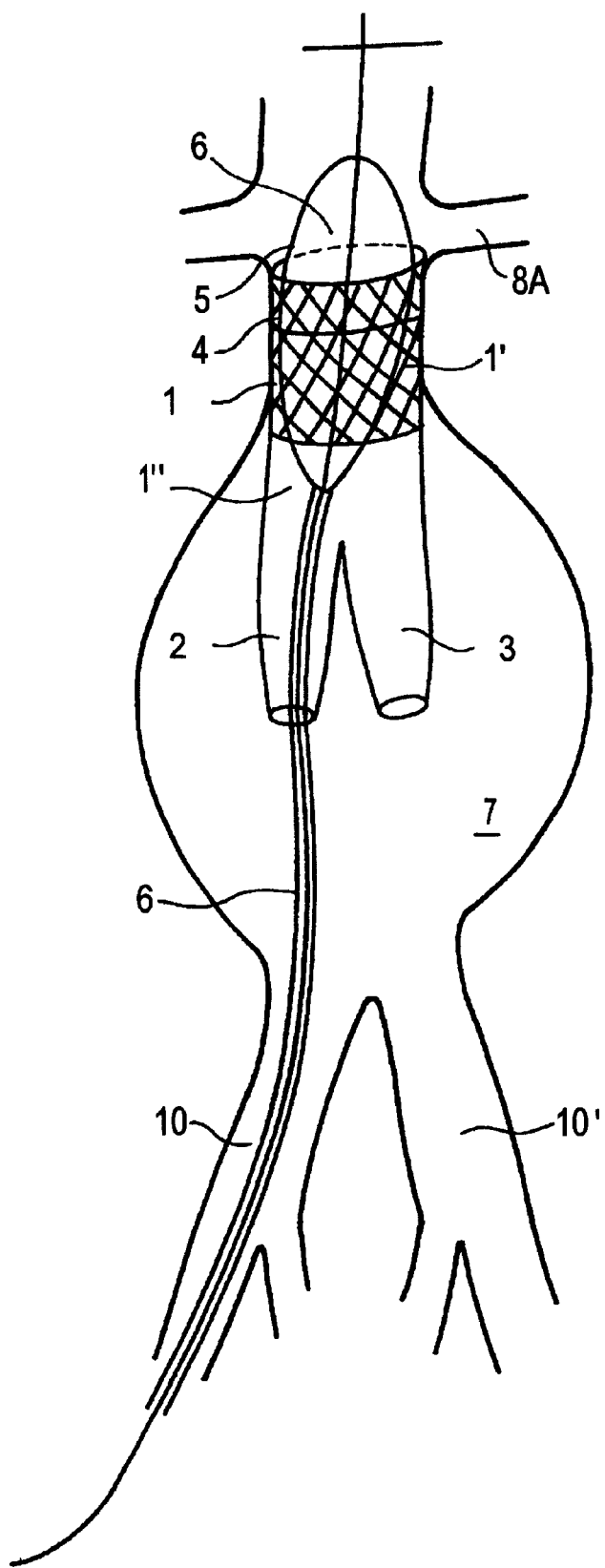
FIG. 1 shows a cross-sectional view of a first embodiment of the invention.

FIG. 1 shows a cross sectional view of a first embodiment of the invention.

The prosthesis has a main branch (1) and two sub-branches (2, 3). The main branch is made up of a tubular section, made from an expandable material such as PTFE and reinforced at the top by an expandable annular section. The middle section (1') of the main branch is made of reinforced PTFE, which extends to the sub-branches (2, 3) via a section (1") made of non-reinforced PTFE. The main branch can be expanded up to a diameter of approximately 28 mm. The proximal end (4) of the main branch is reinforced but a part of the expandable material (PTFE) has been stripped away in order to improve the adherence to the aortic artery. This main branch forms a bifurcation extended by the two free, non-reinforced sub-branches (2, 3). Their cross section reduces slightly to create a conical shape of around 10 mm in diameter at the end, thus improving the distal adherence.

This assembly is mounted onto a guide balloon catheter (6), which allows the main branch to be dilated up to 28 mm, depending on the type of balloon and the insufflation pressure, and the sub-branches are coiled. This prepared assembly is passed via the, iliac artery (10) into the aneurism (7), with the stripped proximal end positioned just below the renal arteries (8). At this point, the main branch (1) is expanded by pressurising the balloon (6). The balloon (6) is then removed, leaving the two sub-branches (2, 3) in the aneurism. These sub-branches (2, 3) are then extended under the pressure of the blood circulation. Each sub-branch (2, 3) of the bifurcation is then extended by means of straight modules of known type, whose length can be altered to suit the adherence to each iliac artery (10, 10').

These straight modules are advantageously expandable modules formed by expandable annular segments encased in an expandable material, such as PTFE.

These modules will be dilated to suit the diameter of the iliac artery.

Figure 2:
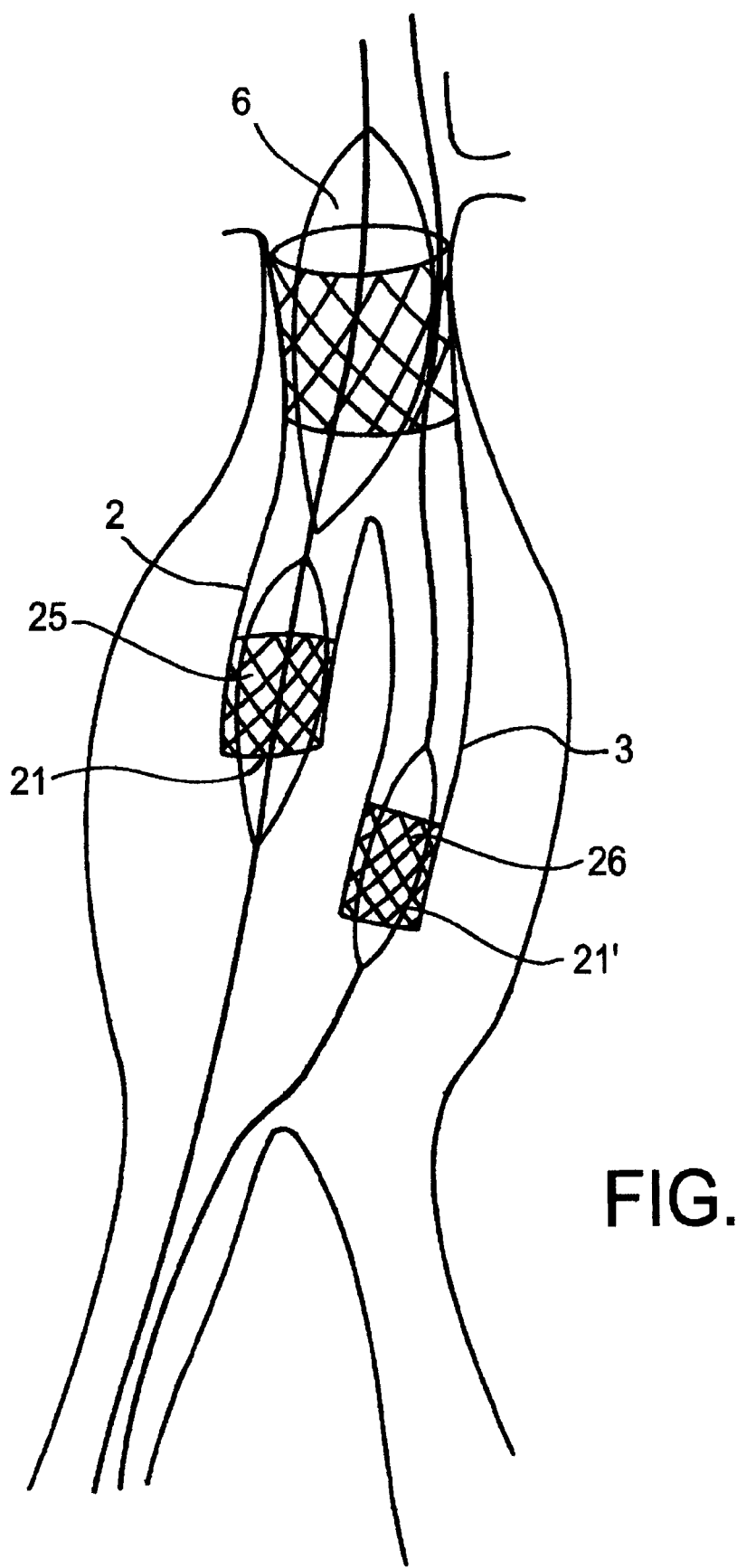
FIG. 2 shows a cross-sectional view of a second embodiment of the invention.

FIG. 2 shows a second embodiment.

The main branch (1) and the two sub-branches (2, 3) are formed of expandable segments encased in an expandable material, such as PTFE. The two sub-branches (2, 3) have longitudinally offset reinforced zones (21, 21') to avoid any overlapping which would result in an excess thickness preventing it from being introduced into the vascular system. Consequently, sub-branch (3) is longer than sub-branch (2). The non-reinforced part of the prosthesis junction can be pre-dilated.

The assembly is mounted onto an expanding device which allows firstly the main branch to be dilated with a main balloon (6) up to 28 mm, depending on the insufflation pressure, then the first sub-branch (2) up to 10 mm using another balloon (25). The second sub-branch (3) is then expanded by means of a third balloon (26). It is also possible to use the same balloon to expand firstly the main branch, then one of the sub-branches.

As previously described, the sub-branches (2, 3) are extended by straight modules (11, 12) formed by annular segments which are adjustable in length encased in an envelope of expandable material, such as PTFE.

Figure 3:
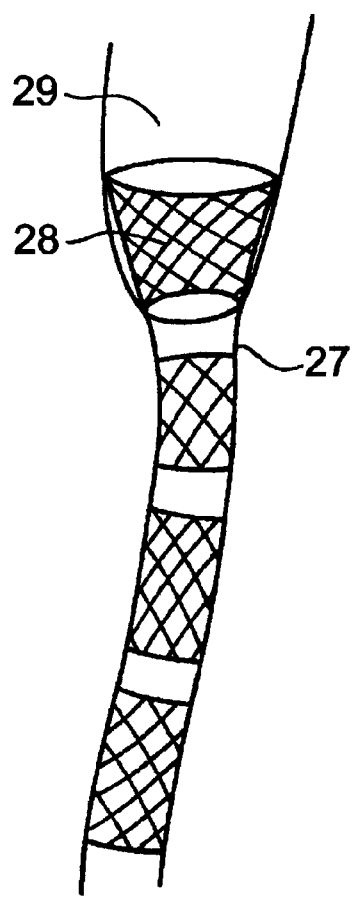
FIGS. 3 and 4 show cross-sectional views of two embodiments of extensions of the sub-branches of the prosthesis.

FIG. 3 shows an embodiment of the extension of the sub-branch where the proximal end of a modular extension (27) has a conical, non-reinforced part (28) connected to the distal end (29) of the main branch.

Figure 4:
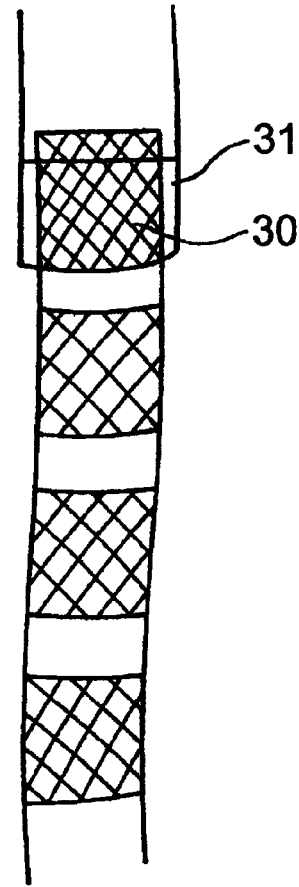

FIG. 4 shows an embodiment of the extension of the sub-branch where the proximal end of a modular extension (27) has a reinforced part (30) connected to the reinforced end (31) of the main branch.

The above descriptive examples of the invention are non-restrictive. The specialist will be able to produce different embodiments without escaping from the inventive concept.

What is claimed is:

1. A bifurcated vascular prosthesis, comprising a tubular main branch extended by at least two sub-branches, wherein:

the main branch is comprised of an expandable material;

at least one part of the main branch has an expandable strengthener in the form of an expandable annular section;

each sub-branch has at least one expandable zone longitudinally offset to avoid overlapping of corresponding longitudinally offset expandable zones between sub-branches; and an end of the main branch opposite to the bifurcation is formed by a partially reinforced tubular section, wherein a part of said expandable material of said tubular section has been stripped away to facilitate adherence to an artery.

2. The prosthesis of claim 1, wherein the main branch is adapted to be expanded up to a diameter of approximately 28 mm, and the sub-branches have a diameter of approximately 10 mm.

3. The prosthesis of claim 1, wherein the main branch is made of reinforced PTFE with one or more expandable annular sections.

4. The prosthesis of claim 1, wherein each sub-branch narrows toward its distal end.

5. The prosthesis of claim 1, wherein the main branch is extended by two reinforced sub-branches having zones that are expandable up to a diameter of approximately 10 mm, the expandable zones being longitudinally offset in order to avoid overlapping of the expandable zones between the two sub-branches, one of the sub-branches being longer than the other.

6. The prosthesis of claim 5, wherein the expandable zones are reinforced with expandable annular sections.

7. The prosthesis of claim 5, wherein the main branch is made of reinforced PTFE with one or more expandable annular sections.

8. The prosthesis of claim 5, wherein each sub-branch narrows towards its distal end.

9. The prosthesis of claim 1, wherein each sub-branch narrows toward its distal end.

10. The prosthesis of claim 1, wherein:

the main branch is made of PTFE reinforced with one or more expandable annular sections; and each sub-branch narrows towards its distal end.

11. The prosthesis of claim 10, wherein:

the main branch is adapted to be expanded up to a diameter of approximately 28 mm, and the sub-branches have a diameter of approximately 10 mm.

* * * * *